United States Patent [19]
Lieberman

[11] 4,026,295
[45] May 31, 1977

[54] SURGICAL KNIFE

[76] Inventor: David M. Lieberman, 9 Prospect Park West, Brooklyn, N.Y. 11215

[22] Filed: June 19, 1975

[21] Appl. No.: 588,287

[52] U.S. Cl. .................................. 128/305; 30/294
[51] Int. Cl.² ..................... A61B 17/32; A61F 9/00
[58] Field of Search ............ 30/168, 289, 290, 294; 128/305, 314

[56] References Cited

UNITED STATES PATENTS

| 159,168 | 1/1875 | Ellis | 30/289 X |
|---|---|---|---|
| 466,343 | 1/1892 | Grant | 30/294 X |
| 1,390,720 | 9/1921 | Powers | 128/305 |
| 1,598,458 | 8/1926 | Sullivan | 30/168 X |
| 3,178,812 | 4/1965 | Lurie | 30/289 X |
| 3,893,238 | 7/1975 | Scholl | 30/289 X |

FOREIGN PATENTS OR APPLICATIONS

| 24,131 | 10/1883 | Germany | 30/294 |
|---|---|---|---|
| 294,427 | 10/1916 | Germany | 30/294 |

Primary Examiner—Channing L. Pace
Attorney, Agent, or Firm—Anthony J. Casella

[57] ABSTRACT

A surgical knife which is particularly adapted to achieve a more precise incision for cataract extraction includes a handle having at one end cutting means in the form of a projecting planar shoe member which is spaced from a pair of projecting ski members, and wherein the cutting blade is disposed perpendicular to the plane of the shoe member, and extends from said shoe member to the space between the ski members. In use, during a cataract operation, the shoe is introduced in the angle created by the iris and the cornea, and is operative to prevent the cutting means or razor blade which is attached perpendicularly to the shoe from encountering the iris and the lens. The spaced skis are positioned outside the eye so as to act as a guide and prevent the surgeon from inadvertently pushing the shoe into the iris or the lens.

12 Claims, 7 Drawing Figures

SURGICAL KNIFE

The subject invention relates to a surgical knife, and more particularly a cataract incision knife by which the operating surgeon can make a better incision to achieve cataract extraction.

There are approximately one-half million cataract operations performed in the United States alone each year. The most common procedure is for the surgeon to make a conjunctival flap utilizing a conventional surgical instrument such as a scissors and forceps. Then the operating surgeon makes an ab-externo incision into the eye with a conventional device, most commonly a keratome or a razor blade; and then the incision is opened for 180° in a circular fashion using a conventional scissors. These scissors are designed for going-left or going-right. After the incision is made, the lens of the eye (which is the cataract) is removed through the open wound. In a conventional cataract operation the entire lens is delivered intercapsularly, i.e., the capsule as well as the contents of the lens is delivered through the incision in toto. Postoperatively, of course, the only means that the patient can see normally would be through an additional optical device.

In a cataract operation, one of the primary considerations is the height and width of the normal surgical zone of the eye, which is on the order of 1-1.5mm and 0.5-1mm, respectively. With respect to this surgical zone, it is extremely important that the incision made by the surgeon be within this zone. From the standpoint of the width of the surgical zone, when viewing the plane of the eye, if the incision is made erroneously extensive damage to the eye can occur. For example, hemorrhage, iris dialysis, or dislocation of the lens may result.

In the conventional technique employing scissors, the primary defect of the incision is associated with the characteristics of a scissors wherein, when the two blades are closed, it is the portion of the scissors closest to the pivot screw which actually cuts. As the scissor is advanced through the eye tissue, the back end of the incision cut becomes jagged, and the scissors cuts the tissue by crushing. In addition, it is extremely difficult, if not impossible, for the surgeon to visualize even with an operating microscope the actual incision as it is being made with the scissors. The surgeon can easily see the tips of the scissors and can only assume that the back end of the scissors is cutting correctly. Most of the time a good surgeon will get a fairly smooth incision with the scissors. If, on the other hand, a stepping or jagged incision by the scissors is achieved, the approximation is not 100% perfect, and the wound can potentially leak. This is the rationale behind the current technique in cataract operations in making small incisions with fewer sutures to close. The more perfect the wound apposition, the earlier theoretically a patient can return to full physical activity.

Essentially, inside the eye there are two structures which obviously the surgeon does not want to damage; one being the iris which an unguarded razor blade can easily cut and result in a major hemorrhage. The second structure is the lens itself, and if the lens capsule is cut, the contents of the cataract can leak out and, postoperatively, the eye is extremely irritated and interferes with the rapid recovery of the patient.

Accordingly, it is a primary object of the subject invention to provide a new and improved apparatus by which the operating surgeon can make a better incision to achieve cataract extraction. Fundamentally, the surgical knife of the subject invention comprises a handle that is attached to a front blade shoe/ski arrangement. The lower portion of the subject device, which is referred to as the shoe member, extends inside the eye. Outside the eye, there are two parallel skis, and vertically inclined between the shoe and between the skis is a razor blade. The device, according to the subject invention, is primarily employed for cataract incision, but at any time the operating surgeon has to make an incision larger than what he would normally make with a razor blade that is unguarded, the incision knife, according to the subject invention, may be employed.

In a cataract operation, the surgeon would first perform an ab-externo incision in one portion of the eye to achieve entrance of the shoe of the subject device into the anterior chamber. The fundamental purpose of the shoe is to prevent the razor blade which is attached perpendicularly to the plane of the shoe from encountering the iris. The two skis which are spaced from the shoe, and which run parallel to the shoe, are set approximately 1.8mm in height from the upper plane of the shoe. During the incision, the skis are outside the eye, and function not only as a guide, but also to prevent the surgeon from inadvertently pushing the shoe into the iris or the lens therebeneath. During the incision, the skis actually ride on the external surface of the eyes thereby providing the surgeon with a precise guage for the depth of the incision. The cutting means, or razor blade, is set perpendicular to the shoe, and runs between the two skies. The razor blade is set back from the tip of the shoe, and encounters the wound to be made under direct visualization of the surgeon through the spacing in the skis. During the incision, the surgical knife device of the subject invention is pushed by the operating surgeon through the area known as the surgical limbus or the surgical zone of the eye. This zone is about ½mm in breath, and hence the ability of the surgeon to constantly visualize the path of the cutting blade of the subject invention is most important in assuring a proper incision. The shoe member of the subject device has a tip portion which is smooth and rounded, and this is important since the tip portion is in direct contact with the iris. The shoe is as thin as possible, and is slightly curved, with the curvature of the shoe generally corresponding to the curvature of the skis that are spaced from the shoe. Likewise, the tips of the skis are also smooth and rounded so as to prevent the tips of the skis from cutting the eye during the incision.

Further details relative to the construction of the subject surgical knife will become apparent from a reading from the detailed description taken in conjunction with the drawings in which.

Figure 1:
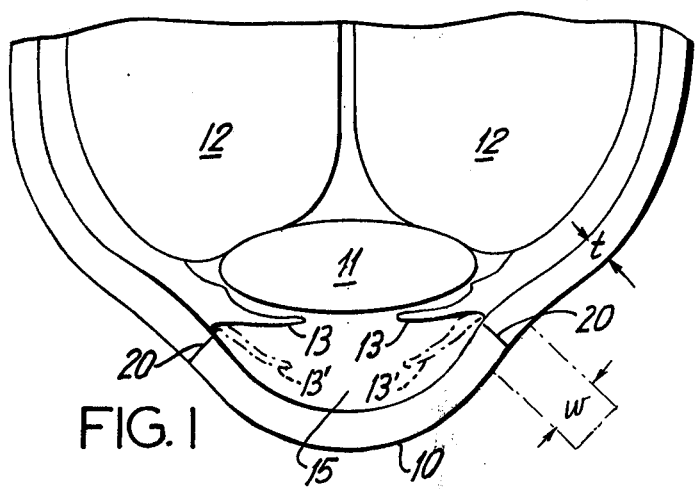
FIG. 1 is a partial sectional view of an eye, and indicating an incision, as well as the surgical zone for a cataract operation.

Referring to FIG. 1, as seen in the cross-section of an eye, lens 11 is positioned between the vitreous humor 12 and the iris 13. The outer portion of the eye includes the cornea 10, and behind the cornea there is the anterior chamber 15. It is noted that at the surgical area the eye is not essentially a perfect circle. The horizontal versus the vertical meridians of the eye are different, with the usual horizontal meridian being 10½mm, while the vertical meridian is 11mm. Thus, any surgical device which would cut a perfect circle would not be suitable for most eyes. Furthermore, a surgical device which does not include a guarded blade must be used with extreme care in the locality of the iris since the iris is paper thin, and is extremely vascular containing very heavy thick wall arterials. Thus, once the iris is cut and is allowed to bleed, the surgeon has no way of obtaining hemostasis which is cautery applied to the vessel to prevent the iris from bleeding further. As indicated above, for removal of the lens 11, an incision is made, as indicated by numeral 20 in FIGS. 1 and 2, which incision extends about 180° of the cornea 10. The cornea is then opened, the iris 13 is retracted to the dotted position indicated at 13' and the lens 11 is removed intact from the eye.

As indicated above, the thickness of the cornea at the surgical zone, indicated by the designation $t$ is on the order of 1.0 to 2mm, whereas the width of the critical zone indicated by the designation $w$ in FIG. 1 is between 0.5mm and 1mm. It is noted that the edge of the cornea is commonly referred to as the sclera, and is in the region of the surgical area of the eye.

Figure 2:
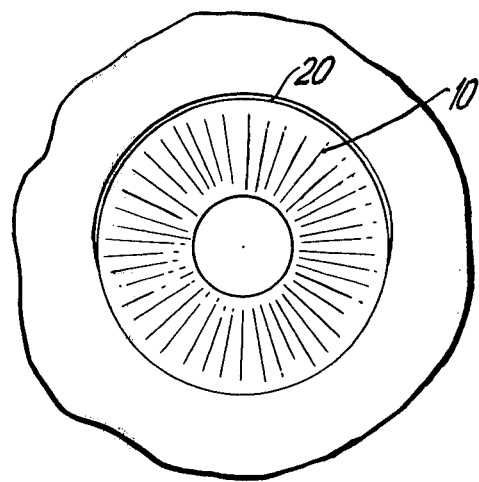
FIG. 2 is a frontal view of an eye, and indicating the 180° incision employed in a cataract operation.
Figure 3:
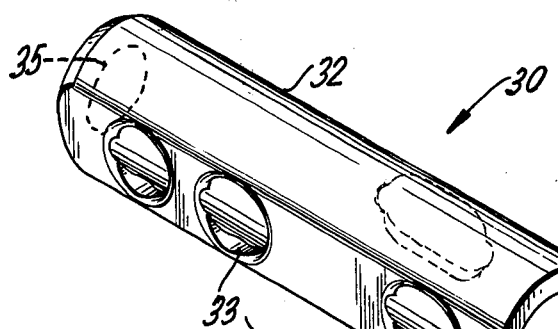
FIG. 3 is a perspective view of a preferred embodiment of a surgical knife made according to the subject invention.

As is readily apparent, because of the relatively small area of the eye in the area of the incision 20, it is most important that the surgical knife employed by the surgeon include means for assisting the surgeon as much as possible in preventing the inadvertent puncturing or cutting of the iris 13, while at the same time affording the surgeon the necessary visibility to insure that the incision be maintained within the critical surgical area $w$ throughout the 180° incision, as viewed in FIG. 2. This is achieved with the surgical knife of the subject invention, a preferred embodiment of which is illustrated in FIGS. 3 through 6, and designated by numeral 30. The surgical knife basically comprises a handle 32 and a cutting means 34 including a cutting blade 40. The handle 32 is generally elongated, preferably of a hollow rigid material such as aluminum, a lightweight metal, and includes side apertures 33 and end aperture 35 for facilitating the handling or gripping of the surgical knife by the surgeon. Of course, the disposition of the apertures may be varied to accommodate left-handed and righthanded surgeons. In addition, the handle 32 may be of solid construction having a suitable cross-section which may be easily gripped by the surgeon for precision guidance of the instrument.

Cutting means 34 is disposed at one end of the handle 32, and a portion of the cutting means may be formed integral or unitary with the handle 32. The projecting end of the cutting means 34 is generally tapered, as shown, and terminates with a projecting planer shoe member 36, and a pair of generally parallel projecting ski members 38, 38 which are spaced from and generally parallel to such shoe member 36. The cutting blade 40 extends between the shoe members 36 and the space intermediate the ski members 38, 38, in a plane generally perpendicular to the plane of the shoe member 36. For accommodating the cutting blade 40, the cutting means 34 may include a slit 42, and the cutting blade may be held in position by means of a screw 44.

Figure 4:
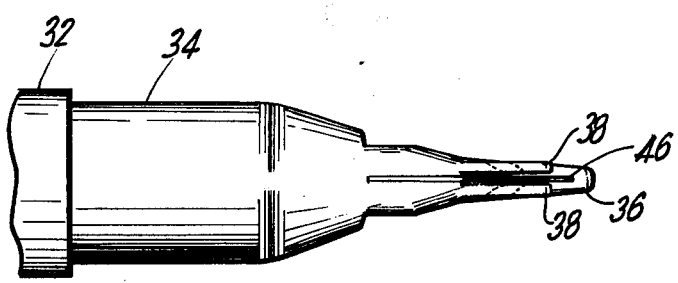
FIG. 4 is a plan view of the cutting means of the subject surgical knife.
Figure 5:
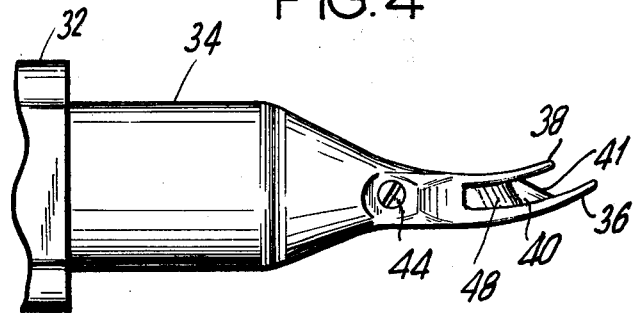
FIG. 5 is a side view of the cutting portion of a surgical knife made according to the subject invention.

As more particularly shown in FIG. 5, the projecting planer shoe member 36 is slightly curved, as are ski members 38, 38, with the radius of the curvature of the shoe member 36 preferably being substantially the same as the radius of curvature of the ski members 38, 38. As more particularly shown in FIG. 4, the projecting tips of the shoe member 36 and the ski members 38, 38 are blunt, and are tapered thereby minimizing the possibility of such projecting members lacerating a portion of the eye during an operation. As also shown in FIG. 4, the surface of the shoe member 36 facing the ski members 38, 38 may be provided with a slot 46 for accommodating the cutting blade 40, and especially for anchoring the position of the cutting blade. As shown in FIG. 5, preferably the cutting blade is inclined rearwardly extending from the projecting end of the shoe member 36 toward the handle, and also, the cutting blade is set back from the projecting tip of the shoe member 36.

As shown in FIGS. 3 through 6, disposed rearwardly of the tapered cutting edge 41 of the cutting blade 40, the cutting means 34 includes rearwardly tapered portions 48 which facilitate the "fanning" of the cornea during the making of the incision. As shown in FIG. 4 preferably the tapered portions 48 extend rearwardly and outwardly from both sides of the cutting blade 40.

In the preferred embodiment of the subject surgical knife 30, the cuttings means, except for the cutting blade, is of unitary construction. However, it is also contemplated that the surgical knife 30 may be made of two inter-meshing pieces which may readily accommodate the cutting blade 40. In addition, although the surgical knife 30 is described as being made of a lightweight metallic material such as aluminum, it may also be made of molded plastic or other suitable material of sufficient rigidity for the intended purpose of the surgical knife 30.

As also illustrated in FIG. 5, the length of the projecting skis 38 is less than the length of the projecting shoe member 36, and the space in between the projecting ski members 38 is sufficiently wide to accommodate the upper portion of the cutting blade 40, and still provide the surgeon with the required visibility in order to insure that the incision 20 is maintained within the surgical zone $w$, as shown in FIG. 1.

Figure 7:
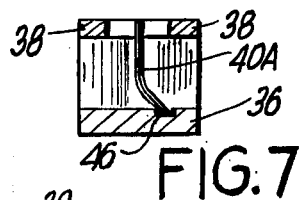
FIG. 7 is a frontal view of a modification of the subject invention.
Figure 6:
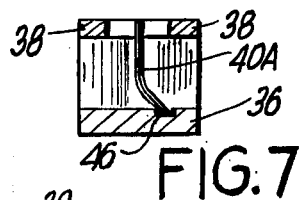
FIG. 6 is a frontal view of the cutting portion of the surgical knife made according to the subject invention.

FIG. 7 illustrates a modification of the subject invention wherein the cutting blade 40A is bent intermediate its height between slot 46 and the skis 38, 38, at an angle of approximately 135°. By this arrangement, the incision 20 results in a two-step incision to achieve a more secure closure of the incision.

In summary there has been described and illustrated a new and improved surgical knife which is specifically adapted for cataract operations. The shoe member 36 of the surgical knife is blunt and has rounded edges, and in operation, the shoe member 36 pushes away the iris and the cataract lens, so that these structures are not incidentally cut. The shoe member is introduced into the eye to a previously made stab incision, and the cutting blade 40, which is located back of the tip of the shoe member 36, engages the wound. The ski members 38, 38, which are on the top of the cutting means 34, engage the outside surface of the eye, thus preventing the shoe member from going too deep inside the eye. Preferably, the ski members 38, 38 are spaced from the projecting planer shoe member 36 a distance on the order of 2mm, corresponding to the maximum thickness of the cornea. The surgical knife is then advanced under the direct visualization of the surgeon in the surgical zone, as illustrated in FIGS. 1 and 2. The 180° incision, designated by numeral 20 in FIG. 2, is perfectly smooth at 90° to the cornea fibers, has no "bumps," and throughout the entire procedure of the incision, the incision is visible to the surgeon by means of the spaced ski members 38, 38.

It will thus be seen that the objects set forth above are efficiently obtained, and since certain changes may be made in the above construction without departing from the spirit and scope of the invention, it is intended that all matter contained in the above description and shown in the accompanying drawings shall be interpreted as illustrative and not a limiting sense. More particularly, it is to be understood that the surgical knife of the subject invention can be used any time the surgeon wishes to limit the depth of a cut, such as the cutting of a specific tissue without cutting the underlying structures. Possible uses of the surgical knife of the subject invention in surgery, and its subspecialties are as follows:

1. In neurosurgery the subject invention may be employed for cutting of the dura mater, for the separating of dura from arachnoid or in the separating of the arachnoid membrane from the pia membrane.

2. For plastic surgery, the surgical knife may be employed for cutting of skin grafts from the host, or in the removal of sutures wherein the shoe member functions to insure that the skin is not pierced.

3. In ophthalmic surgery, as indicated above it may be employed in cataract incisions, and the surgical knife of the subject invention may be also employed in the performance of scleral flaps or in lamellar disections.

4. In orthopedic surgery, the surgical knife may be employed in the cutting of the synovial membrane, or the opening of the bursal sacs.

5. For general surgery, the surgical knife of the subject invention may be employed in enucleation of cysts, or in incising the peritoneum.

6. In the field of vascular surgery, the subject surgical knife may be employed in separating the adventitia from the muscularis, or in endarterectomy.

7. In gynecological surgery, the surgical knife may be employed in separating the dermis from the epidermis and in ectopic pregnancies.

I claim:

1. A surgical knife comprising:
   an elongated handle, one end of which is adapted to be manually gripped;
   cutting means disposed at and axially aligned with the opposite end of said handle, said cutting means having upper and lower portions including a lower elongated arcuate shoe member projecting axially from said opposite end of the handle, a pair of upper spaced, elongated ski members also projecting axially from said opposite end of the handle, said elongated ski members being generally arcuate in configuration to conform to the configuration of said shoe member, said elongated ski members being disposed above and spaced from said shoe member; and
   an elongated generally upwardly facing cutting blade having a cutting edge and extending generally axially with and contacting said shoe member, said cutting blade extending intermediate said spaced ski members for a portion of their length whereby the cutting edge thereof is visible through the space intermediate the ski members.

2. A surgical knife as in claim 1 wherein said shoe member is generally flat in a direction transverse to a plane extending between the upper and lower portions of the cutting means, and wherein said cutting blade extends generally perpendicular to the flattened portion of the shoe member.

3. A surgical knife as in claim 1 wherein the length of the skis are less than the projecting length of said shoe member.

4. A surgical knife as in claim 1 wherein cutting blade includes an intermediate bend between the shoe and the space intermediate the ski members.

5. A surgical knife as in claim 1 wherein the projecting tip of the shoe member is blunt.

6. A surgical knife as in claim 1 wherein the projecting ends of the ski members are blunt.

7. A surgical knife as in claim 1 wherein the cutting edge of the cutting blade is inclined in the direction extending from the top of the projecting shoe member to the handle.

8. A surgical knife as in claim 1 wherein the cutting means includes a tapered portion extending between said shoe member and said ski members intermediate the cutting edge of the cutting blade and said opposite end of the handle.

9. A surgical knife as in claim 1 wherein the handle is elongated, and the cutting means are disposed generally parallel to the longitudinal axis of said handle.

10. A surgical knife as in claim 1 wherein the handle is provided with apertures for facilitating gripping of the surgical knife.

11. A surgical knife as in claim 1 wherein said cutting blade is removably secured to the cutting means.

12. A surgical knife as in claim 1 wherein the cutting means, except for the cutting blade, is of unitary construction.

* * * * *